United States Patent [19]
Cannon

[11] Patent Number: 4,560,376
[45] Date of Patent: Dec. 24, 1985

[54] ANAL MEDICATION APPLICATOR

[76] Inventor: Joseph P. Cannon, 4440 W. 95th St., Oak Lawn, Ill. 60453

[21] Appl. No.: 571,367

[22] Filed: Jan. 16, 1984

[51] Int. Cl.[4] .............................................. A61M 5/00
[52] U.S. Cl. ..................................................... 604/54
[58] Field of Search ................ 128/341, 343; 604/218, 604/239, 187, 57, 58, 54

[56] References Cited

U.S. PATENT DOCUMENTS

| | | | |
|---|---|---|---|
| 719,487 | 2/1903 | Minor | 128/341 |
| 1,750,272 | 3/1930 | Kirk | 128/343 |
| 2,631,586 | 3/1953 | Reilly | 128/341 X |
| 3,077,194 | 2/1963 | Walden et al. | 128/343 |

*Primary Examiner*—John D. Yasko
*Attorney, Agent, or Firm*—Silverman, Cass & Singer, Ltd.

[57] ABSTRACT

An applicator for positively directing discharge of medication only to an especially sensory circumferential area of the anal canal immediately inside the anus.

4 Claims, 5 Drawing Figures

ANAL MEDICATION APPLICATOR

BACKGROUND OF THE INVENTION

This invention relates generally to medication dispensing devices, and more particularly, relates to devices for application of anal medication.

Anal medication, such as hemorrhoidal ointment and foam have been administered by inserting syringe-type devices through the anus into the rectal canal where the medication is discharged. Since only the circumferential area immediately inside the anus extending for approximately 3 centimeters into the lower rectal vault is supplied with sensory perception, the medication dispensed by prior art syringe devices has generally been wasted in the nonsensory area located deeper into the rectal canal. Such deeper areas of the rectal canal have only sympathatic and para sympathatic nerves. Typical prior art syringe devices supplied with hemorrhoidal ointments and foam such as Americaine ® and Proctofoam ®, respectively, have an opening in the terminal end of the dispensing tube through which the bulk of the medication is discharged into the rectal canal. Even when such tubes have been provided with lateral openings, the resulting limited volume of medication discharged through the lateral openings impacts too remote from the lower rectal vault for application directly to the sensory anal area where the base of internal hemorrhoids may be located.

Other syringe-type devices for insertion into body orifices are described in U.S. Pat. Nos. 719,487, 1,127,201, 2,036,218 and 3,593,713, but none of these devices is designed to provide discharge of medication to the limited sensory area immediately inside the anus. For example, U.S. Pat. No. 3,593,713 describes a catheter tube having an area of perforations along its length and an elastic casing or sheath which can be rolled back to expose the desired length of perforated area. The length of perforated area is controlled to suit requirements for discharge of medication along different lengths to accommodate, for example, variation in the length of the urethra. The catheter is also provided with an inflatable chamber located beyond the perforated area of the barrel and rearwardly of its tip, so that when the chamber is inflated, it will engage the wall within the body orifice in which the catheter is inserted to retain the catheter in place.

U.S. Pat. No. 1,127,201 describes a syringe for use as a douche which has perforations in the end and along the length of the barrel. A rubber guard can be adjustably positioned along the length of the barrel to limit penetration into the womb. In use, the apex of the guard limits the penetrating length of the syringe to between 2 and 4 inches. None of the syringes described in these patents provides structure to specifically limit discharged medication to the sensory area immediately within the anus.

SUMMARY OF THE INVENTION

The anal medication applicator according to this invention, provides for the medication to be specifically directed to the sensory area of the anal canal immediately within 3 centimeters of the anus.

The applicator includes a syringe-type barrel of plastic or other suitable material, having a cylindrical wall which is closed at the end inserted into the anus. A stop means is fixed on the barrel to engage the user's anal canal. The cylindrical wall of the barrel is provided with a plurality of lateral apertures therethrough. The apertures are located within approximately 2.5 centimeters measured along the wall from the stop means toward the closed end of the barrel. Since the end of the barrel is closed, the medication is forced to discharge laterally through the apertures directly against the sensory area of the first 3 centimeters within the mucosa of the anus.

In a preferred embodiment, the stop means of the applicator includes a flange which circumferentially extends from the barrel and engages the user's anus. A convenient, manually operated plunger is provided for forcing the discharge of the medication laterally from the barrel through the apertures after the barrel has been inserted through the anus to the extent limited by engagement of the anus with the circumferential flange. Consequently, the medication is specifically directed to the sensory area of anal pathology such as external hemorrhoid, Crohn's Disease, pruritus and similar anal infections, as well as the base of internal hemorrhoids. None of the medication is wasted by longitudinal discharge further into the nonsensory portion of the rectal canal.

DESCRIPTION OF THE PREFERRED EMBODIMENTS

Figure 1:
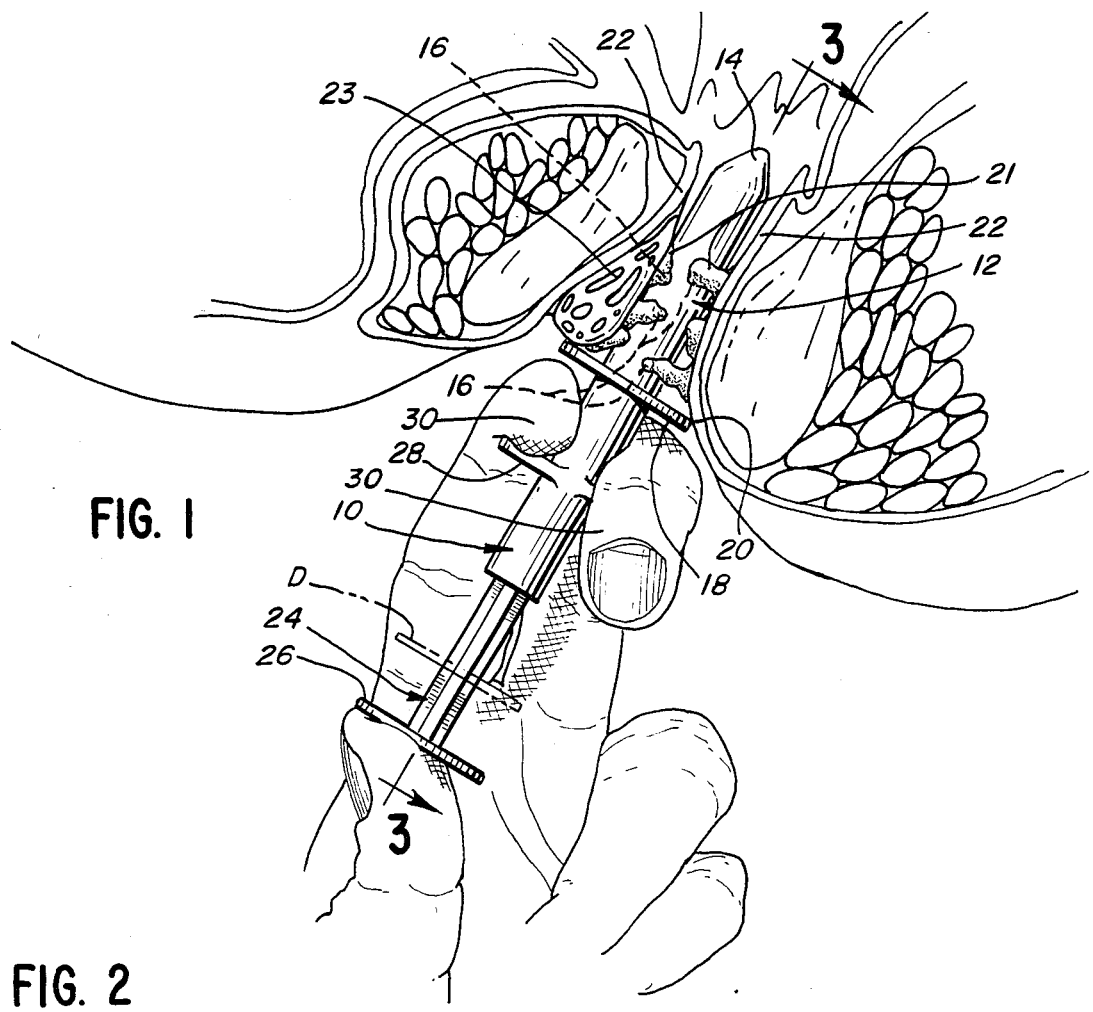
FIG. 1 is a perspective view of the manual insertion of an embodiment of the anal medication applicator according to this invention, illustrating the closed end of the applicator and discharge of the medication laterally to the mucosa immediately inside the anus illustrated in section.
Figure 3:
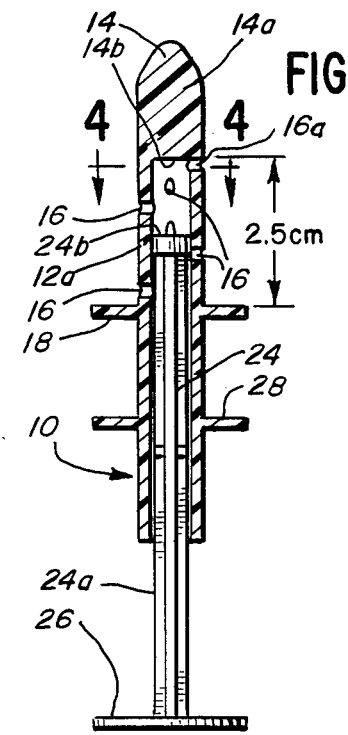
FIG. 3 is a sectional view taken along the line 3—3 in FIG. 1 and in the indicated direction, illustrating the lateral apertures of the device which are located within 2.5 centimeters from the stop flange which engages the anus to limit the position of the apertures and discharge of the medication therethrough in FIG. 1.

Referring to FIGS. 1 and 3, an embodiment of the anal medication applicator of the invention is designated generally by reference character 10. The syringe-type applicator 10 includes a barrel 12 with a closed end 14. As best shown in FIG. 3, the barrel 12 has multiple, radially and longitudinally distributed apertures 16 through the cylindrical wall 12a.

Figure 4:
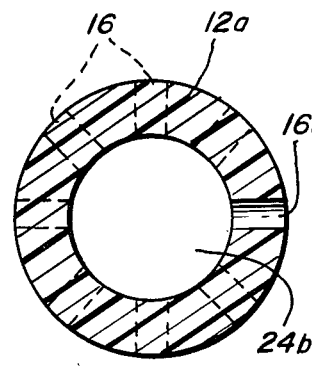
FIG. 4 is an enlarged sectional view taken along line 4—4 in FIG. 3, and in the indicated direction, illustrating the radial distribution of the lateral apertures.

Preferably, the apertures 16 are radially distributed over substantially the entire circumference of the barrel wall 12a as shown in FIG. 4. Referring again to FIGS. 1 and 3, the apertures 16 are longitudinally distributed along the length of the barrel 12 between tip 14 and a circumferential stop flange 18. The flange 18 is located on the barrel for engagement with the user's anus 20, as illustrated in FIG. 1. The superior medicinal effectiveness of the applicator 10 is provided not only by the closed tip 14, but in addition, all of the apertures 16 are longitudinally distributed within 2.5 centimeters along the length of the barrel 12 measured from the stop flange 18 toward the tip 14. As a result of this specifically limited spacing of the apertures 16 from the flange 18, the engagement of the flange 18 with the anus 20 not only limits the penetrating length of the barrel 12 through the anus, but also limits the position of the apertures 16 so that the medication 21 is discharged directly to the sensory portion of the side walls 22 of the anal canal, and external hemorrhoid 23, which is located within the first three centimeters immediately within the anus 20.

Figure 2:
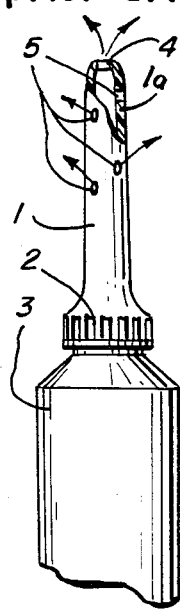
FIG. 2 is a side view of a prior art anal medication applicator, partially broken away, illustrating a nozzle having an opening in the end and side perforations adjacent thereto.

In contrast to the cooperation and spacing of the flange 18 and lateral apertures 16 to specifically limit discharged medication to the sensory area immediately within the anus, FIG. 2 illustrates a prior art dispenser comprising a nozzle 1 which is supplied with commercial, hemorrhoidal ointment (Americaine ®). Nozzle 1 has a flared base 2 which is threaded onto a supply tube 3 of the ointment. The nozzle has an open end 4 through which the bulk of the ointment is longitudinally discharged, as indicated by arrows, into the rectal canal. The nozzle 1 also has a plurality of apertures 5 through the side wall 1a and are located within approximately 1 inch from the larger end opening 4. Ointment which is not discharged through the primary, end opening 4 can be discharged through the smaller side wall openings 5; however, since the nozzle is approximately 2 inches in length from the base 2 to the open end 4, even the small amount of ointment discharged through the apertures 5 is directed generally beyond the sensory area immediately inside the anus even if the nozzle 1 is not entirely inserted with the base 2 against the anus.

Referring again to FIGS. 1 and 3, the applicator 10 is provided with a plunger 24 having a thumb rest 26 which is manually depressed into the barrel 12 to force discharge of the medication through the apertures 16 as shown in FIG. 1. As illustrated, the plunge 24 is formed as a ribbed shaft along the portion 24a immediately extending from the thumb rest 26. To assist the manual operation of the applicator 10, a finger flange 28 is provided on the barrel 12 to allow positioning of the user's fingers 30 between the finger flange 28 and the stop flange 18 which engages the anus 20 during the depression of the plunger 24.

Referring to FIG. 3, the barrel 12 is provided with a filled or solid portion 14a which extends rearwardly from the closed tip 14 and terminates in an end wall 14b positioned transverse of the wall 12a and located adjacent the aperture 16a which is most remote from flange 18. Wall 14b confines the fluid medication to the volume within the barrel 12 adjacent the apertures 16, and wall 14b forms a stop to engage the end 24b of the plunger 24 upon full depression thereof.

Referring to FIG. 1, the loaded applicator 10 is arranged so that the smoothly rounded tip 14 can be gently inserted to open and dilate the anus 20. When the barrel 12 is fully inserted, the flange 18 will engage the anus to prevent further penetration of the barrel 12 into the rectum and position the apertures 16 within approximately 2.5 centimeters from the anus 20. When the plunger 24 is then depressed to the dotted line position illustrated at D, the medication is laterally discharged through the apertures 16 directly to the sensory portion of the side walls 22 within 3 centimeters from the anus 20. As a result, none of the medication is wasted by discharge longitudinally further into the rectal cavity to impinge upon the nonsensory portion of the rectal canal.

Figure 5:
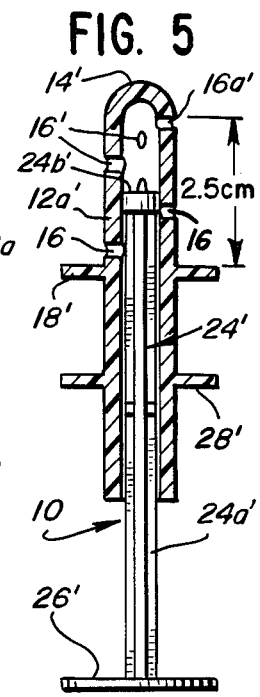
FIG. 5 is a sectional view of a modified embodiment of the anal medication applicator according to this invention, illustrating an abbreviated, closed tip in relation to the lateral apertures, as compared to the embodiment of FIG. 3.

Referring to FIG. 5, a second embodiment of the applicator of this invention is designated generally by reference character 10'. The parts of applicator 10' correspond to the parts of applicator 10 in FIG. 3 with the exception that the closed tip 14' extends only a short distance from the adjacent aperture 16a'. As a result, the solid portion 14a and wall 14b illustrated in FIG. 3 are not necessary in the applicator 10' because the interior surface of the tip 14' provides confinement of the fluid medication adjacent the apertures 16' and also provides a stop to engage the end 24a' of the plunger 24' upon full depression thereof. In addition, the abbreviated tip 14' will extend a shorter distance into the anal canal when the flange 18' engages the user's anus, in comparison to the corresponding extension of tip 14 on applicator 10.

Variations in the size and structural features of cooperating parts and in materials used may occur to the skilled artisan without departing from the crux of the invention, the scope of which is set forth in the claims hereto appended.

I claim:

1. An applicator for dispensing anal medication to the sensory portion of an anal canal, comprising:
   A. a syringe-type barrel having a cylindrical wall closed at one end thereof;
   B. stop means fixed on said barrel for engagement with a user's anus to limit the length of penetration of said barrel into the user's anal canal;
   C. a plurality of lateral apertures through said cylindrical wall, said apertures being located within approximately 2.5 centimeters measured along the wall from said stop means toward said closed end, for limiting discharge of medication to the sensory portion of said anal canal adjacent said stop means; and
   D. expelling means for forcing discharge of said medication laterally from the barrel through said apertures.

2. The applicator as claimed in claim 1, in which said stop means comprises a flange circumferentially extending from said cylindrical wall.

3. The applicator as claimed in claim 1, in which said closed end includes an end wall extending transverse to said cylindrical wall and adjacent to the aperture located most remote from said stop means.

4. An applicator for dispensing anal medication to the sensory portion of an anal canal, comprising:
   A. a syringe-type barrel having a cylindrical wall closed at one end thereof;
   B. stop means fixed on said barrel for engagement with a user's anus to limit the length of penetration of said barrel into the user's anal canal to provide a predetermined segment of the barrel disposed in the canal;
   C. a plurality of lateral apertures through said cylindrical wall of said barrel segment, said apertures being arranged in concentric, axially spaced apart circumferential rings on said segment located within approximately 2.5 centimeters measured along the wall from said stop means toward said closed end, for limiting discharge of medication to the sensory portion of said anal canal adjacent said stop means; and
   D. expelling means for forcing discharge of said medication laterally from the barrel through said apertures over said sensory portion.

* * * * *